United States Patent
Shah et al.

(10) Patent No.: US 6,299,980 B1
(45) Date of Patent: Oct. 9, 2001

(54) ONE STEP LUBRICIOUS COATING

(75) Inventors: Chirag B. Shah, Nashua, NH (US); Eugene Tedeschi, Still River, MA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 09/163,038

(22) Filed: Sep. 29, 1998

(51) Int. Cl.$^7$ .................................................. B32B 27/40
(52) U.S. Cl. ................................................. 428/423.1
(58) Field of Search ........................ 428/423.1, 423.3, 428/423.7, 423.9, 424.8, 424.5, 425.6, 425.9

(56) References Cited

U.S. PATENT DOCUMENTS

| | | | |
|---|---|---|---|
| 3,632,557 * | 1/1972 | Brode et al. | 260/77.5 |
| 4,373,009 | 2/1983 | Winn | 428/424.2 |
| 4,585,666 | 4/1986 | Lambert | 427/2 |
| 4,625,012 * | 11/1986 | Rizk et al. | 528/28 |
| 5,032,666 | 7/1991 | Hu et al. | 528/70 |
| 5,040,544 | 8/1991 | Lessar et al. | 128/784 |
| 5,134,192 | 7/1992 | Feijen et al. | 525/54.1 |
| 5,405,919 | 4/1995 | Keefer et al. | 525/377 |
| 5,470,307 | 11/1995 | Lindall | 604/20 |
| 5,512,055 | 4/1996 | Domb et al. | 604/265 |
| 5,525,348 | 6/1996 | Whitbourne et al. | 424/423 |
| 5,525,357 | 6/1996 | Keefer et al. | 424/486 |
| 5,605,696 | 2/1997 | Eury et al. | 424/423 |
| 5,612,052 | 3/1997 | Shalaby | 424/426 |
| 5,645,931 | 7/1997 | Fan et al. | 428/334 |
| 5,662,960 | 9/1997 | Hostettler et al. | 427/2.3 |
| 5,674,192 | 10/1997 | Sahatjian et al. | 604/28 |
| 5,676,963 | 10/1997 | Keefer et al. | 424/423 |
| 5,698,738 | 12/1997 | Garfield et al. | 564/112 |
| 5,718,892 | 2/1998 | Keefer et al. | 424/78.27 |
| 5,770,229 | 6/1998 | Tanihara et al. | 424/488 |
| 5,770,645 | 6/1998 | Stamler et al. | 524/419 |
| 5,776,611 | 7/1998 | Elton et al. | 428/423.1 |
| 5,797,887 | 8/1998 | Rosen et al. | 604/265 |
| 5,849,368 | 12/1998 | Hostettler et al. | 427/536 |
| 5,919,570 | 7/1999 | Hostettler et al. | 428/424.8 |

FOREIGN PATENT DOCUMENTS

| 0 352 295 B1 | 1/1990 | (EP) . |
| 0 357 401 B1 | 3/1990 | (EP) . |
| 0 397 784 B1 | 11/1990 | (EP) . |

* cited by examiner

Primary Examiner—Blaine Copenheaver
Assistant Examiner—Christopher Paulraj
(74) Attorney, Agent, or Firm—Oppenheimer Wolff & Donnelly LLP

(57) ABSTRACT

A coating is provided comprising a polyurethane network formed from the reaction on a substrate to be coated, of a mixture comprising a polyisocyanate; a hydroxyl donor and/or amine donor; a polymer selected from the group consisting of polyethylene oxide, polyvinyl pyrrolidone, polyvinyl alcohol, polyethylene glycol, and polyacrylic acid; and an isocyanatosilane adduct having terminal isocyanate groups and at least one hydrolyzable alkoxy group bonded to silicon in a solvent. A method for preparing the coating is also provided.

18 Claims, No Drawings

ONE STEP LUBRICIOUS COATING

FIELD OF THE INVENTION

This invention relates to a lubricious coating which may be applied to a substrate in one step, comprising a polyisocyanate; a hydroxyl donor and/or amine donor; a polymer selected from the group consisting of polyethylene oxide, polyvinyl pyrrolidone, polyvinyl alcohol, polyethylene glycol, and polyacrylic acid; and an isocyanatosilane adduct having terminal isocyanate groups and at least one hydrolyzable alkoxy group bonded to silicon. The invention also relates to a method for producing the lubricious coating.

BACKGROUND OF THE INVENTION

It has long been known that hydrophilic coatings with low friction (coefficient of friction of 0.3 or less) are useful for a variety of medical devices such as catheters, catheter introducers and the like. When low friction surfaces are used, the devices, upon introduction into the body, slide easily within arteries, veins and other body orifices and passageways. There have been a wide variety of methods used to provide the surfaces desired. In some cases the material of the catheter or medical device is formed of a material having good anti-friction properties such as poly (tetrafluoroethylene) or other plastics which tend to avoid abrasion with the body. However, in many cases the selection of materials does not provide the anti-slip properties desired in conjunction with other desirable properties for the particular medical device.

Prior art hydrophilic coatings typically rely on a two step, two coating process, usually involving a primer coat of isocyanate or isocyanate/polymer blend which is dried, followed by a second coat containing at least one hydrophilic polymer such as polyvinyl pyrrolidone or polyethylene oxide. The two coatings, one superimposed on the other, are then baked to effect a cure. This forms an interpolymer complex or a network including the hydrophilic polymer. Several disadvantages to this process exist.

First, the exact ratio of primer material to the hydrophilic polymer is difficult to control, as it depends on whatever amounts of primer and hydrophilic polymer happen to be deposited by the wet film during the respective coating steps. Second, the primer may begin to redissolve in the second coating solution, causing some loss of primer and further resulting in difficulty in controlling the primer/hydrophilic polymer ratio. Third, the hydrophilic polymer is not covalently bonded to the substrate and may bond to other materials in the area leading the coating to lose its desired properties. Fourth, additional facilities and time are needed for coating with a two step process, as compared to a one step process.

Prior patents have suggested applying solutions of polyvinylpyrrolidone with isocyanate and/or polyurethane in multi-step operations. These coatings often lack good durability. For example, U.S. Pat. No. 4,585,666 issued to Lambert discloses medical devices having hydrophilic coatings formed from an isocyanate layer overcoated with a polyvinylpyrrolidone layer. However, the multistep procedure makes it difficult to tailor the properties and values of the final coatings.

U.S. Pat. No. 4,625,012, Rizk et al., describes a one step method for preparing moisture curable polyurethane polymers having pendant alkoxysilane groups and isocyanate terminals on a substrate. The method includes reacting an isocyanatosilane adduct and an isocyanate different from the isocyanatosilane with a polyol. The isocyanatosilane adduct and the isocyanate have at least two isocyanato groups each. Furthermore, the isocyanatosilane is produced by reacting an isocyanate having at least three isocyanato groups with an organofunctional alkoxysilane. The coating formed, however, is not lubricious.

In U.S. Pat. No. 4,373,009, Winn, a coating process for preparing a lubricious coating is disclosed. A coupling agent is first applied to the substrate. A coating is then applied on top of the coupling agent. The coupling agent bonds the coating to the substrate. Although the coupling agent and coating may be applied to the substrate from the same solution, the preferred method is to apply them separately.

U.S. Pat. No. 5,645,931, Fan et al., describes a one step coating process for preparing a thromboresistant lubricious coating. The coating is comprised of a substantially homogeneous composite of polyethylene oxide and polyisocyanate in an inert solvent. However, the one step coating process is only suitable for polymeric substrates.

U.S. Pat. No. 5,662,960, Hostettler et al., describes a process for producing slippery, tenaciously adhering hydrogel coatings containing a polyurethane-polyurea (PU/PUR) hydrogel commingled with a poly(N-vinyl pyrolidone) hydrogel. The coating may be applied on plastic, rubber, or metallic substrates. However, the process is performed in several steps. Initially, plastic substrates are activated by oxidative chemical treatments and plasma treatments with oxygen or nitrogen containing plasma gases. Metallic substrates are treated with aminosilane primers. Then, a base coat of PU/PUR hydrogel is applied to the substrate followed by the application of a coat of a second hydrogel.

The present invention provides a one step coating which may be applied in a single step, alleviates the need for a primer or coupling agent, and can be applied on various substrates, including, but not limited to, plastics and metals.

SUMMARY OF THE INVENTION

The present invention provides a coating comprising a polyurethane network formed from the reaction, on a substrate to be coated, of a mixture comprising a polyisocyanate; a hydroxyl donor and/or amine donor; a polymer selected from the group consisting of polyethylene oxide, polyvinyl pyrrolidone, polyvinyl alcohol, polyethylene glycol, and polyacrylic acid; and an isocyanatosilane adduct having terminal isocyanate groups and at least one hydrolyzable alkoxy group bonded to silicon in a solvent.

According to another embodiment of the present invention, an article is provided comprising a substrate on which a coating is formed comprising a polyurethane network formed from the reaction, on a substrate to be coated, of a mixture comprising a polyisocyanate; a hydroxyl donor and/or amine donor; a polymer selected from the group consisting of polyethylene oxide, polyvinyl pyrrolidone, polyvinyl alcohol, polyethylene glycol, and polyacrylic acid; and an isocyanatosilane adduct having terminal isocyanate groups and at least one hydrolyzable alkoxy group bonded to silicon, in a solvent.

According to yet another embodiment of the invention, a method of preparing a coating on a substrate to be coated comprises forming a mixture of a polyisocyanate, a hydroxyl donor and/or amine donor; a polymer selected from the group consisting of polyethylene oxide, polyvinyl pyrrolidone, polyvinyl alcohol, polyethylene glycol, and polyacrylic acid; and an isocyanatosilane adduct having terminal isocyanate groups and at least one hydrolyzable alkoxy group bonded to silicon, in a solvent; applying the mixture to the substrate; and curing the mixture on the substrate to form the coating.

These and other features and objects of the invention are more fully appreciated from the following detailed description of a preferred embodiment of the invention.

DETAILED DESCRIPTION OF A PREFERRED EMBODIMENT

According to the present invention, a lubricious coating is formed from the reaction, on a substrate to be coated, of a mixture comprising a polyisocyanate; a hydroxyl donor and/or an amine donor; a polymer selected from the group consisting of polyethylene oxide, polyvinyl pyrrolidone, polyvinyl alcohol, polyethylene glycol, and polyacrylic acid; and an isocyanatosilane adduct having terminal isocyanate groups and at least one hydrolyzable alkoxy group bonded to silicon; in a solvent. The resulting coating is highly lubricious, thromboresistant, anti-microbial, and drug eluting.

It is believed that the isocyanate functional groups of the polyisocyanate and isocyanatosilane react with the hydroxyl donor to create a polyurethane network and react with the amine donor to form a polyurea network. Furthermore, the silane groups of the isocyanatosilane are believed to form covalent bonds with the substrate to which the coating is applied when cured in the presence of moisture to form a strongly adherent coating.

The coating mixture in solution is prepared by weighing the appropriate quantities of polyisocyanate; hydroxyl donor and/or amine donor; a polymer selected from the group consisting of polyethylene oxide, polyvinyl pyrrolidone, polyvinyl alcohol, polyethylene glycol, and polyacrylic acid; and isocyanatosilane adduct and adding them into an appropriate mixing vessel. Additional solvents may be added to adjust the viscosity of the mixture. The choice of ingredients in the coating mixture also affects the physical properties of the overall coating. Solids contents in a range of from about 0.2 to about 0.25% are preferred. This solution is mixed well and then applied to an appropriate substrate such as catheter tubes, medical tubing introducers, polymer coated medical wires, stents, and dilatation balloons, by conventional coating application methods. Such methods include, but are not limited to, dipping, spraying, wiping, painting, and the like.

The materials of construction of a suitable substrate include, but are not limited to, polymers, metal, glass, ceramics, composites, and multilayer laminates of the aforementioned materials.

After applying the coating solution, the solvent is preferably allowed to evaporate from the coated substrate, such as by exposure to ambient conditions for at least 5 minutes.

The coating is subsequently cured. The cure time, temperature, and humidity vary with the choice of polyisocyanate; polyol and polyamine; isocyanatosilane adduct; and the composition of the substrate. The curing rate may be increased by the addition of small amounts water to the coating mixture prior to applying the coating to the substrate.

Cure temperatures may range from about 75° F. to about 350° F. Cure times may range from about 2 minutes to about 72 hours, depending upon the cure temperature and the reactivity of the polyisocyanate, hydroxyl donor, amine donor, and isocyanatosilane adduct. In all cases the cure conditions should be non-deleterious to the underlying substrate.

After the coating is cured, it is preferable to rinse or soak the coating in water to remove any uncomplexed polymers. Generally, a brief rinse of 10–15 seconds is sufficient, however, a longer rinse or soak is acceptable since the coating is cured and forms a stable gel when in contact with water. After rinsing, the coating may be dried either at ambient conditions, or at elevated temperatures.

After the coating is formed, the coating can imbibe water from an aqueous solution prior to introduction to the body and can become lubricious. Alternatively, the coating can imbibe water solely from body fluids, even if not exposed to water prior to introduction into the body. Because the coating is a cross-linked system, it adheres well to the substrate even when hydrated. The coating retains its lubricating properties even after subsequent drying and rehydration. If the coating is to be used in a body related application, such as in catheters, introducer tubes and the like, the materials selected should be compatible with the body and non-toxic to the body. Biocompatible materials include, but are not limited to, polyethylene, polypropylene, polyurethane, naturally occurring polymers, stainless steel and other alloys.

The coating may be applied to various substrates, including, but not limited to, metals, ceramics, plastics, and glass.

The coating may be applied to metal substrates such as the stainless steel used for guide wires and other devices.

Organic substrates which may be coated with the coatings of this invention include, but are not limited to, polyether block amide, polyethylene terephthalate, polyetherurethane, polyesterurethane, other polyurethanes, natural rubber, rubber latex, synthetic rubbers, polyester-polyether copolymers, polycarbonates, and other organic materials. Some of these materials are available under various trademarks such as Pebax™ available from Atochem, Inc. of Glen Rock, N.J.; Mylar™ available from E.I. duPont deNemours and Co. of Wilmington, Del.; Texin™ 985A from Bayer Corporation of Pittsburgh, Pa.; Pellethane™ available from Dow Chemical of Midland, Mich.; and Lexan™ available from General Electric Company of Pittsfield, Mass.

The polyisocyanate is preferably an aromatic polyisocyanate. More preferably, the polyisocyanate is an aromatic polyisocyanate based on toluene diisocyanate and is dissolved in propylene glycol monomethyl acetate and xylene. Preferably, the amount of polyisocyanate ranges from about 0.2 to about 10 percent by weight based upon 100% total weight of coating mixture.

The hydroxyl donor is preferably a polyol. Polyols useful in this invention may be any of a large number of polyols reactive with the polyisocyanate and isocyanatosilane to form a polyurethane network. Examples of suitable polyols include, but are not limited to, polyester polyols, polyether polyols, modified polyether polyols, polyester ether polyols, castor oil polyols, and polyacrylate polyols, including Desmophen™ A450, A365, and A160 available from Bayer Corporation. Preferred polyols include castor oil and castor oil derivatives (triglyceride of 12-hydroxyoleic acid) such as DB oil, Polycin™ 12, Polycin™ 55, and Polycin™ 99F available from CasChem, Inc. of Bayonne, N.J. More preferably, the polyol is polyester based, such as Desmophen™ 1800. Suitable diols include, but are not limited to, poly(ethylene adipates), poly(diethyleneglycol adipates), polycaprolactone diols and polycaprolactone-polyadipate copolymer diols, poly(ethyleneterephthalate) polyols, polycarbonate diols, polytetramethylene ether glycol, ethyleneoxide adducts of polypropylene triols. Suitable products include Desmophen™ 651A-65, 1300-75 and 800 available from Bayer Corporation of Pittsburgh, Pa., Niax™ E-59 and others available from Union Carbide of Danbury, Conn., Desmophen™ 550 DU, 1600U, I920D, and 1150 available from Bayer Corporation. Many other polyols are available and may be used as known to those skilled in the art.

An amine donor may be incorporated in the mixture in addition to or in lieu of the hydroxyl donor. Preferred amine donors include triethylene glycolamine which has the formula $H_2NCH_2CH_2OCH_2CH_2OCH_2CH_2NH_2$ and an approximate molecular weight of about 148 available as Jeffamine™ XTJ-504 from Huntsman Corp., Salt Lake City, Utah; polyetherdiamines such as Jeffamine™ XTJ-500 and XTJ-501 which have a predominantly polyethylene oxide backbone and an approximate molecular weight of 600 and 900, respectively, available from Huntsman Corp., Salt Lake City, Utah; polyethertriamines such as Jeffamine™ T-403 which is a polypropylene oxide-based triamine and has an approximate molecular weight of 440 available from Huntsman Corp., Salt Lake City, Utah; and amine terminated polypropyleneglycols such as Jeffamine D-400 and Jeffamine™ D-2000 which have approximate molecular weights of 400 and 2000, respectively. Other amine donors include urethane modified melamine polyols containing amine and hydroxyl groups available as Cylink HPC™ from Lytec Industries, West Patterson, N.J.

Coating solutions containing amine donors are typically easier to process, cure quicker, and form more rigid and lower viscosity coatings than coating solutions containing hydroxyl donors and no amine donors. Coating solutions containing amine donors, however, typically have a shorter pot life and form less flexible coatings than coating solutions containing hydroxyl donors.

Hydroxyl donors in the coating solution cause formation of a polyurethane. In contrast, amine donors in the coating solution cause formation of a polyurea network. A polyurea network may provide better biocompatibility and stability than a polyurethane network since chain cleavage does not occur. Further, polyurea networks typically have better network properties, such as fatigue resistance, than polyurethane networks.

The amount of hydroxyl donor and amine donor in the coating mixture may be varied to obtain desirable surface properties for the coating. For example, the hydroxyl donor and amine donor may be varied to obtain a desired lubricity. Preferably, the amount of hydroxyl donor ranges from about 0.2 to about 10 percent by weight and the amount of amine donor ranges from about 0.2 to about 10 percent by weight based upon 100% total weight of coating mixture.

Preferably, the polymer selected from the group consisting of polyethylene oxide, polyvinyl pyrrolidone, polyvinyl alcohol, polyethylene glycol, and polyacrylic acid is polyethylene oxide. More preferably, the polymer is polyethylene oxide having a viscosity average molecular weight of about 300,000, such as Polyox™ available from Union Carbide Corp of South Charleston, W.Va. The polymer preferably has a mean molecular weight of from about 100,000 to about 2,000,000, Preferably, the amount of the polymer ranges from about 0.2 to about 20 percent by weight based upon 100% total weight of coating mixture.

The isocyanatosilane adduct has one or more unreacted isocyanate functional groups. An isocyanatosilane having two or more unreacted isocyanate functional groups may be produced by reacting a silane, such as aminosilane or mercaptosilane, with polyisocyanate. The isocyanatosilane has at least one hydrozable alkoxy bonded to silicon. Preferably, the amount of isocyanatosilane ranges from about 0.1 to about 10 percent by weight based upon 100% total weight of coating mixture.

The solvent should not react with the polyisocyanate; hydroxyl donor; amine donor; polymer selected from the group consisting of polyethylene oxide, polyvinyl pyrrolidone, polyvinyl alcohol, polyethylene glycol, and polyacrylic acid; or isocyanatosilane adduct but is a solvent for all the components of the mixture. The solvent is preferably free of reactive amine, hydroxyl and carboxyl groups. Suitable solvents include, but are not limited to, methylene chloride, tetrahydrofuran (THF), acetonitrile, chloroform, dichloroethane, dichloroethylene, and methylene bromide. Preferably, the solvent is acetonitrile and THF, especially with a ratio of acetonitrile to THF of about 3:1.

Wetting agents may be added to the coating solution to improve wettability to hydrophobic surfaces. Wetting agents include, but are not limited to, fluorinated alkyl esters, such as Fluorad™ FC-430 available from 3M Corp., and octylphenol ethylene oxide condensates, such as Triton™ X-100 available from Union Carbide. A preferred concentration of wetting agent in the coating solution is from about 0.01 to about 0.2% by weight based upon 100% solids in the coating solution.

Viscosity and flow control agents may be added to the coating mixture to adjust the viscosity and thixotropy of the mixture to a desired level. Preferably, the viscosity is such that the coating may be formed on the substrate at the desired thickness. Viscosities of from about 50 cps to about 500 cps may be used although higher or lower viscosities may be useful in certain instances. Viscosity control agents include, but are not limited to, fumed silica, cellulose acetate butyrate, and ethyl acrylate/2-ethyl hexyl acrylate copolymer. Flow control agents are preferably present in amounts of from about 0.05 to about 5 percent by weight based upon 100% total weight of coating mixture.

Antioxidants may be added to the coating mixture to improve oxidative stability of the cured coatings. Antioxidants include, but are not limited to, tris(3,5-di-t-butyl-4-hydroxy benzyl) isocyanurate, 2,2'-methylenebis (4-methyl-6-t-butyl phenol), 1,3,5-trimethyl-2,4,6-tris (3,5-di-t-butyl-4-hydroxybenzyl) benzene, butyl hydroxy toluene, octadecyl 3.5 di-t-butyl-4-hydroxyhydrocinnamate, 4,4 methylenebis (2,6-di-butylphenol), p,p'-dioctyl diphenylamine, and 1,1,3-tris-(2-methyl-4-hydroxy-5-t-butylphenyl) butane. Antioxidants are preferably present in amounts from 0.01 to 1 percent by weight based upon 100% total weight of coating mixture.

Conventional pigments may be added to the coating mixture to impart color or radiopacity, or to improve the appearance of the coatings.

Air release agents or defoamers which are optionally included in the coating solution include, but are not limited to, polydimethyl siloxanes, 2,4,7,9-tetramethyl-5-decyn-4, 7-diol, 2-ethylhexyl alcohol, and n-beta-aminoethyl-gamma-amino-propyl trimethoxysilane. Air release agents are preferably added in amounts from 0.005 to 0.5 percent by weight based upon 100% total weight of coating mixture.

The following non-limiting examples are meant to be illustrative embodiments of the present invention.

EXAMPLE 1

A coating solution was prepared by combining the following ingredients and mixing them thoroughly:
  (a) 0.32 g. of an aromatic polyisocyanate adduct based on toluene diisocyanate and dissolved in propylene glycol monomethyl acetate and xylene having an NCO content of about 10.5% and a molecular weight of about 400 available as Desmodur™ CB 60 from Bayer Corporation;

(b) 0.67 g. of a solvent-free, saturated polyester resin (polyol) available as Desmophen™ 1800 from Bayer Corporation;

(c) 0.91 g. of polyethylene oxide available as Polyox™ having a molecular weight of about 300,000 from Union Carbide Corp., (d) 76.97 g. acetonitrile;

(e) 21.82 g. THF; and (f) 2.02 g. 3-isocyanyopropyltriethoxysilane available as UCT I7840-KG from United Chemical Technologies, Bristol, Pa.

Five 18" inch wires were coated with the solution by dipping for 11 seconds. The solvent was evaporated at ambient conditions for approximately 20 minutes. The wires were then placed in an oven at 40° C. for 10 hours to cure the coating.

Upon removal from the oven, the wires were rinsed in water and dried.

The coating was tested by ASTM D 1894-87 Standard Test Methods for Static and Kinetic Coefficients of Friction of Plastic Film and Sheeting.

While a preferred embodiment of the present invention has been described, it should be understood that various changes, adaptations and modifications may be made therein without departing from the spirit of the invention and the scope of the appended claims.

What is claimed is:

1. An article comprising a substrate on which is coated a coating formed from the reaction on the substrate, of a mixture comprising (a) a polyisocyanate, (b) a member selected from the group consisting of a hydroxyl donor, an amine donor and any combination thereof, (c) a polymer selected from the group consisting of polyethylene oxide, polyvinyl pyrrolidone, polyvinyl alcohol, polyethylene glycol, and polyacrylic acid, and (d) an isocyanatosilane adduct having terminal isocyanate groups and at least one hydrolyzable alkoxy group bonded to silicon, in a solvent;

wherein said article is a medical device and said coating is suitable for reducing the coefficient of friction of said medical device when said medical device is in contact with a body fluid.

2. An article according to claim 1 wherein said substrate is selected from the group consisting of plastic and metal.

3. An article according to claim 1, wherein said polyisocyanate is an aromatic polyisocyanate based on toluene diisocyanate.

4. An article according to claim 1, wherein said hydroxyl donor is a polyol.

5. An article according to claim 4, wherein said polyol is a saturated polyester polyol.

6. An article according to claim 1, wherein said isocyanatosilane adduct is 3-isocyanatopropyltriethoxysilane.

7. An article according to claim 1, wherein said solvent comprises at least one chemical selected from the group consisting of tetrahydrofuran, acetonitrile, and methylene chloride.

8. An article according to claim 7, wherein said solvent comprises tetrahydrofuran and acetonitrile.

9. An article according to claim 1, wherein said polymer is polyethylene oxide.

10. An article according to claim 9, wherein said polyethylene oxide has a viscosity average molecular weight of about 300,000.

11. An article according to claim 1, wherein said polymer is polyvinyl pyrrolidone.

12. An article according to claim 1, wherein said polymer is polyacrylic acid.

13. An article according to claim 1, wherein said polymer is polyvinyl alcohol.

14. An article according to claim 1, wherein said polymer is polyethylene glycol.

15. An article according to claim 1, wherein said polyisocyanate is present in an amount from about 0.2 to about 10 percent by weight of said mixture.

16. An article according to claim 1, wherein said polymer is present in an amount from about 0.2 to about 20 percent by weight of said mixture.

17. An article according to claim 1, wherein said isocyanatosilane is present in an amount from about 0.1 to about 10 percent by weight of said mixture.

18. An article according to claim 1, wherein said hydroxyl donor, said amine donor or said mixture of hydroxyl donor and amine donor is present in an amount from about 0.2 to about 10 percent by weight of said mixture.

* * * * *